United States Patent [19]

Guerrant et al.

[11] Patent Number: 5,436,239

[45] Date of Patent: Jul. 25, 1995

[54] METHOD OF TREATING CLOSTRIDIUM DIFFICILE COLITIS AND CHOLERA

[75] Inventors: Richard L. Guerrant; Guodong Fang; Manasses C. Fonteles, all of Charlottesville, Va.

[73] Assignee: The University of Virginia Patent Foundation, Charlottesville, Va.

[21] Appl. No.: 40,444

[22] Filed: Apr. 1, 1993

Related U.S. Application Data

[63] Continuation-in-part of Ser. No. 861,620, Apr. 1, 1992, abandoned.

[51] Int. Cl.$^6$ .................. A61K 31/34; A61K 31/405; A61K 31/44; A61K 31/55
[52] U.S. Cl. .................. 514/219; 514/342; 514/420; 514/468
[58] Field of Search .............. 514/219, 420, 468, 342

[56] References Cited

PUBLICATIONS

Wallace et al., J. Lipid Mediators, 1(1), 13–23, 1989.

*Primary Examiner*—Marianne M. Cintins
*Assistant Examiner*—Phyllis G. Spivack
*Attorney, Agent, or Firm*—Sheldon H. Parker

[57] ABSTRACT

The invention relates to the treatment of antibiotic associated colitis, typically due to *Clostridium difficile* using the Platelet Activating Factor antagonists WEB 2170, SR 27417 or BN 52021, or the cyclooxygenase antagonist indomethacin. The PAF antagonists BN 52021 and SR 27417 and the cyclooxygenase antagonist indomethacin were effective in inhibiting the secretory effects caused by *C. difficile* Toxin A and by Cholera toxin.

10 Claims, 7 Drawing Sheets

* vs Toxin A alone, p<0.0001

FIGURE 1 when comparing with Toxin A, p<0.001; *p<0.01.

FIGURE 3

| Rabbits with toxin A & PBS | | Rabbits with toxin A+AA & PBS | | |
|---|---|---|---|---|
| Loops with Toxin A | Loops with PBS | Loops with Toxin A + AA | Loops with Toxin A adjacent to AA | Loops with PBS |
| (n=6) | (n=6) | (n=5) | (n=5) | (n=6) |
| 0.574 | 0.009 | 0.012 | 0.007 | 0.070 |
| 0.431 | 0.009 | 0.167 | 0.127 | 0.089 |
| 0.700 | 0.020 | 0.164 | 0.200 | 0.300 |
| 0.625 | 0.020 | 0.011 | 0.000 | 0.140 |
| 0.775 | 0.067 | 0.060 | 0.000 | 0.000 |
| 0.750 | 0.100 | | | 0.000 |
| mean 0.643 | 0.037 | 0.083 | 0.069 | 0.100 |
| SD 0.128 | 0.037 | 0.078 | 0.090 | 0.112 |

| Toxin A (n=39) | PBS (n=38) | Toxin A + BN (n=13) | Toxin A + WEB (n=6) | Toxin A + SR n=(9) | Toxin A /SR n=(6) | Toxin A + INDO n=(5) |
|---|---|---|---|---|---|---|
| 0.044 | 0.011 | 0.000 | 0.025 | 0.094 | 0.075 | 0.080 |
| 0.104 | 0.000 | 0.058 | 0.040 | 0.070 | 0.111 | 0.020 |
| 0.081 | 0.010 | 0.106 | 0.060 | 0.125 | 0.100 | 0.000 |
| 0.175 | 0.000 | 0.060 | 0.040 | 0.133 | 0.086 | 0.070 |
| 0.176 | 0.050 | 0.043 | 0.020 | 0.125 | 0.125 | 0.061 |
| 0.186 | 0.067 | 0.056 | 0.033 | 0.114 | 0.200 | |
| 0.115 | 0.060 | 0.073 | | 0.125 | | |
| 0.278 | 0.022 | 0.128 | | 0.146 | | |
| 0.173 | 0.050 | 0.060 | | 0.091 | | |
| 0.111 | 0.020 | 0.057 | | | | |
| 0.143 | 0.017 | 0.067 | | | | |
| 0.229 | 0.020 | 0.060 | | | | |
| 0.233 | 0.009 | 0.080 | | | | |
| 0.185 | 0.013 | | | | | |
| 0.300 | 0.000 | | | | | |
| 0.140 | 0.021 | | | | | |
| 0.150 | 0.016 | | | | | |
| 0.277 | 0.159 | | | | | |
| 0.343 | 0.056 | | | | | |
| 0.280 | 0.022 | | | | | |
| 0.180 | 0.050 | | | | | |
| 0.367 | 0.067 | | | | | |
| 0.236 | 0.025 | | | | | |
| 0.236 | 0.056 | | | | | |
| 0.255 | 0.010 | | | | | |
| 0.356 | 0.009 | | | | | |
| 0.375 | 0.009 | | | | | |
| 0.300 | 0.021 | | | | | |
| 0.286 | 0.040 | | | | | |
| 0.371 | 0.008 | | | | | |
| 0.356 | 0.044 | | | | | |
| 0.240 | 0.030 | | | | | |
| 0.222 | 0.067 | | | | | |
| 0.222 | 0.055 | | | | | |
| 0.200 | 0.225 | | | | | |
| 0.200 | 0.140 | | | | | |
| 0.200 | 0.009 | | | | | |
| 0.180 | 0.008 | | | | | |
| 0.200 | | | | | | |
| Mean | | | | | | |
| 0.223 | 0.039 | 0.065 | 0.036 | 0.114 | 0.116 | 0.046 |
| SD | | | | | | |
| 0.084 | 0.046 | 0.030 | 0.014 | 0.024 | 0.045 | 0.034 |

FIGURE 4 vs Toxin alone: *p=0.015; **p=0.008.

| Rabbits with toxin A & PBS | | Rabbits with toxin A+quinacrine & PBS | | |
|---|---|---|---|---|
| Loops with Toxin A (n=15) | Loops with PBS (n=15) | Loops with Toxin A + QN (n=11) | Loops with Toxin A adjacent to QN (n=11) | Loops with PBS (n=11) |
| 0.106 | 0.02 | 0.02 | 0.051 | 0.02 |
| 0.514 | 0.02 | 0.104 | 0.025 | 0.02 |
| 0.204 | 0.032 | 0.326 | 0.46 | 0.124 |
| 0.143 | 0.032 | 0.3 | 0.104 | 0.124 |
| 0.25 | 0.029 | 0.255 | 0.043 | 0.023 |
| 0.261 | 0.029 | 0.213 | 0.001 | 0.023 |
| 0.4 | 0.029 | 0.07 | 0.083 | 0.03 |
| 0.96 | 0.029 | 0.071 | 0.083 | 0.03 |
| 0.143 | 0.054 | 0.02 | 0.05 | 0 |
| 0.175 | 0.054 | 0.09 | 0.05 | 0 |
| 0.209 | 0.054 | 0.02 | 0.11 | 0 |
| 0.225 | 0.054 | | | |
| 1.25 | 0.28 | | | |
| 1.13 | 0.14 | | | |
| 0.92 | 0 | | | |
| Mean 0.459 | 0.057 | 0.135 | 0.097 | 0.036 |
| SD 0.398 | 0.069 | 0.116 | 0.124 | 0.045 |
| SEM 0.103 | 0.018 | 0.035 | 0.037 | 0.014 |

FIGURE 6

|  |   | \multicolumn{6}{c}{Resistance} |
| --- | --- | --- | --- | --- | --- | --- | --- |
|  |   | 5h | 6h | 7h | 8h | 9h | 10h |
| ToxinA | 1 | 0.521 | 0.425 | 0.353 | 0.301 | 0.220 | 0.189 |
|  | 2 | 0.596 | 0.544 | 0.495 | 0.448 | 0.360 | 0.321 |
| QN |   | 0.807 | 0.804 | 0.791 | 0.791 | 0.788 | 0.768 |
| Tx+QN | 1 | 0.827 | 0.799 | 0.728 | 0.638 | 0.489 | 0.458 |
|  | 2 | 0.825 | 0.758 | 0.679 | 0.615 | 0.533 | 0.493 |
| PBS |   | 0.801 | 0.787 | 0.814 | 0.797 | 0.794 | 0.794 |

Toxin A 1,2 both = 0.02ug (0.07 ug/ml)

QN = quinacrine $2 \times 10^{-5}$ M.

(Toxin A + QN) 1,2 both = Toxin A 0.02ug + quinacrine $2 \times 10^{-5}$ M.

METHOD OF TREATING CLOSTRIDIUM DIFFICILE COLITIS AND CHOLERA

CROSS REFERENCE TO RELATED APPLICATIONS

This application is a continuation-in-part of Ser. No. 7/861,620 filed Apr. 1, 1992 now abandoned.

FIELD OF THE INVENTION

The invention relates to the treatment of antibiotic associated colitis, typically due to *Clostridium difficile* using Platelet Activating Factor antagonists, such as WEB 2170, SR 27417 or BN 52021, or the cyclooxygenase antagonists, such as indomethacin. The PAF antagonists BN 52021 and SR 27417 and the cyclooxygenase antagonist indomethacin were effective in inhibiting the secretory effects caused by *C. difficle* Toxin A and even by Cholera toxin.

BACKGROUND OF THE INVENTION

*Clostridium difficile* is one of the most frequently recognized bacterial causes of diarrheal disease in hospitalized adults in industrialized countries. The microorganism can be acquired nosocomially and is present in environmental sources. Antibiotic associated colitis and pseudomembranous colitis are frequently associated with cytotoxigenic *Clostridium difficile*. The frequency of *Clostridium difficile* toxin associated with antibiotic associated colitis is 50-80% and with pseudomembranous colitis is 90-100%. Despite available treatment for antibiotic associated colitis and pseudomembranous colitis, relapses occur in 20-25% of patients. Vancomycin and metronidazole can be effective, but are subject to relapse after the use of the drugs may occur.

*Clostridium difficile* produces two toxins, A (enterotoxic) and B (cytopathic), the former (Toxin A) being implicated in the pathogenesis of pseudomembranous colitis. Toxin A causes hemorrhagic fluid accumulation associated with mucosal damage and a cytopathic effect in tissue culture cells. In experimental animals such as rabbits, toxin A causes hemorrhagic fluid secretion and cell damage in ligated intestinal segments of loops, and is considered to be the cause of antibiotic-associated colitis in experimental hamsters and in people.

Toxin B is a more potent cytotoxin than toxin A, but it has no enterotoxic activity. It has been reported that the toxin A is important in the pathogenesis of *Clostridium difficile* disease. In animal models of the disease, *Clostridium difficile* culture supernatant filtrate or purified toxin A causes mucosal lesions characteristic of antibiotic-associated colitis. In human disease, as well as in animal models, a spectrum of mucosal changes ranging from nonspecific colitis (with or without diarrhea) to severe disease with complete mucosal necrosis has been described in prior literature.

Antibiotics, including vancomycin or metronidazole, directed against *C. difficile*, or anion exchange resins that bind the toxins of *C. difficile*, including cholestyramine, have been used to treat *C. difficile* diarrhea. However, the antibiotics prolong carriage of *C. difficile* and relapses are common and resins are not always well tolerated.

PAF inhibitors have been have been found to be effective in treating Inflammatory Bowel Disease (IBD) when administered 4-7 days after the induction of colitis. The PAF inhibitor BN52021, however, shows no effect in the first four days. *Chemical Abstracts* 110:190302k (1989). IBD is distinct from the specific *Clostridium difficile* toxin-induced antibiotic associated acute colitis. IBD, including Crohn's disease, is a chronic, recurring, granulomatous inflammatory process that is largely related to host susceptibility. *C. difficile* diarrhea is a specific, acute, toxin-mediated diarrhea that can occur in any individual and does not recur over many years as is characteristic of IBD. *Clostridium difficile* is defined as "a species that is part of the normal colon flora in human infants and sometimes in adults. It sometimes produces a toxin that causes pseudomembranous enterocolitis in patients receiving antibiotic therapy" Dorland's Illustrated Medical Dictionary, W. B. Saunders Co., Philadelphia, Pa., 27th Edition, 1988, p. 348. Pseudomembranous enterocolitis is defined as "an acute inflammation of the bowel muscosa with the formation of pseudomembranous plaques overlying an area of superficial ulceration, and the passage of the pseudomembranous material in the feces; it may result from shock and ischemia or be associated with antibiotic therapy." Dorland's Illustrated Medical Dictionary, supra, p. 560. Crohn's disease is defined as "a chronic granulomatous inflammatory disease of unknown etiology, involving any part of the gastrointestinal tract from mouth to anus, but commonly involving the terminal ileum with scarring and thickening of the bowel wall; it frequently leads to intestinal obstruction and fistula and abscess formation and has a high rate of recurrence after treatment." Dorland's Illustrated Medical Dictionary, supra, p. 484. IBD is, to an extent, susceptible to control by diet, fitness and stress reduction. Eating Right for a Bad Gut: The Complete Nutritional Guide to Ileitis, Colitis, Crohn's Disease & Inflammatory Bowel Disease, Dr. James Scala, Penguin.

SUMMARY OF THE INVENTION

It has now been found that the hemorrhagic fluid secretion caused by *Clostridium difficile* toxin A in ligated intestinal segments can be significantly blocked by administering an effective amount of either a Platelet Activating Factor (PAF) inhibitor, or by a cyclooxygenase inhibitor, or by the combination of inhibitors. The PAF inhibitors are from the group consisting of BN52021, WEB 2170 or SR27417. The phospholipase $A_2$ inhibitor is from the group consisting of aristolochic acid, bromophenacyl bromide and quinacrine. The cyclooxygenase inhibitor is indomethacin.

The fluid secretion caused by Cholera toxin in ligated intestinal segments can be blocked by administering an effective amount of a Platelet Activating Factor inhibitor selected from the group consisting of BN52021 and SR27417 or the cyclooxygenase inhibitor indomethacin. The combination of the cyclooxygenase inhibitor indomethacin and at least one Platelet Activating Factor antagonist from the group consisting of SR 27417 and BN 52021 also blocks the hemorrhagic fluid secretion caused by Cholera toxin.

BRIEF DESCRIPTION OF THE DRAWINGS

The specification and disclosed invention will be better understood when read in reference to the drawings in which.

DETAIL DESCRIPTION OF THE PREFERRED EMBODIMENTS

The hemorrhagic fluid secretion caused by *Clostridium difficile* toxin A in ligated intestinal segments can be significantly blocked by either Platelet Activating Factor (PAF) inhibitors BN52021, WEB 2170, SR27417; phospholipase $A_2$ inhibitors, Aristolochic Acid, Quinacrine, and bromophenacyl bromide or by cyclooxygenase inhibitor indomethacin, or by the combustion of BN 52021 or WEB 2170 and indomethacin.

*CRC Handbook of PAF and PAF Antagonists*, Edited by Braquet, CRC Press, Boston, Mass., identifies WEB 2170 on page 51. The ginkgolide BN 52021 (IHB nomenclature) is illustrated on page 52 of the CRC Handbook, the subject matter of the CRC Handbook being incorporated herein by reference as though completely reproduced.

The structural formula for SR 27417 is as follows:

The structural formula for BN 52021, with $R^1$ and $R^2$ equal OH end $R^3$ equals H, is as follows The structural formula for WEB 52170, is as follows:

The availability of highly purified *Clostridium difficile* toxin A, has allowed accurate, reproducable study of the specific effects involved in early mucosal damage and its correlation with the intestinal response. The preparation of toxin A and the use of toxin A in studies in ligated small intestinal segments and other studies, is disclosed in *Laboratory Investigation*, Vol. 61, No. 4, 1989, pages 419 through 425, *Clostridium difficile* Toxin A, Lima et al., the subject matter of which is incorporated herein by reference, as though completely reproduced.

The instant disclosure conducted tests using: (1) platelet activating factor (PAF) inhibitors, BN52021 (BN), WEB2170 (WEB) and SR27417 (SR); (2) the phospholipase $A_2$ inhibitors, aristolochic acid (AA), Quinacrine (QN) and bromophenacyl bromide (BPB); and (3) cyclooxygenase inhibitor, indomethacin (INDO). These were tested both in vivo in the rabbit ileal ligated loop model and in vitro in monolayers of T-84 cells in tissue culture (a colonic epithelial carcinoma cell line) to determine the effects of these inhibitors on the cytotoxicity and secretory responses due to *C. difficile* toxin A.

EXPERIMENT I

*Clostridium difficile* toxin A alone and in combination with the inhibitors were placed in 4–6 cm ligated Ileal segments in 1.5–2.5 kg, male, New Zealand white rabbits. The rabbits were fasted overnight and provided water ad libitum. The animals were anesthetized with an initial intramuscular dose of ketamine (35 mg/kg body weight) and xylazine (5 mg/kg). Ligated rabbit small intestinal segments of approximately 5 cm were made with double ties of umbilical tape. These segments were injected with the following combinations and then returned to the abdominal cavity without separation from the remaining intestine or interruption of the blood supply. After six (6) hours the animals were sacrificed and the fluid volume (milliliters) and length (centimeters) for each loop was measured and a volume to length ratio calculated. Toxin A 10 μg/segment in 1 ml consistently caused severe hemorrhagic inflammatory fluid secretion at 6–8 hours (V/L=0.64±0.13 ml/cm segment, n=6). The molarity (M) indicates the drug concentration in the 1 ml containing the 10 μg/ml Toxin A. Phosphate buffered saline (PBS) is used as a control.

Each rabbit was injected with one of the following:
1 ml toxin A in PBS (10 μg/ml)
1 ml PBS (as a control),
1 ml toxin A and BN52021 ($10^{-4}$M and $10^{-5}$) [BN]
1 ml toxin A and WEB2170 ($10^{-5}$M and $10^{-6}$M) [WEB]
1 ml toxin A and SR27417 ($10^{-5}$ and $10^{-6}$M) [SR]
1 ml toxin A and Aristolochic acid ($10^{-5}$M) [AA]
1 ml toxin A and a combination of quinacrine ($10^{-5}$M) [QN], indomethacin ($10^{-5}$M) [INDO]
1 ml toxin A and bromophenacyl bromide ($10^{-5}$) [BPB]
0.5 ml toxin A (20 μg/ml) plus 0.5 ml of BN ($2 \times 10^{-4}$M and $2 \times 10^{-5}$)
0.5 ml toxin A and WEB ($2 \times 10^{-5}$M and $2 \times 10^{-6}$)
0.5 ml toxin A and SR ($2 \times 10^{-5}$M and $2 \times 10^{-6}$)
0.5 ml toxin A and AA ($2 \times 10^{-5}$M)
0.5 ml toxin A and QN ($2 \times 10^{-5}$M)
0.5 ml toxin A and INDO ($2 \times 10^{-5}$M)

Figure 1:
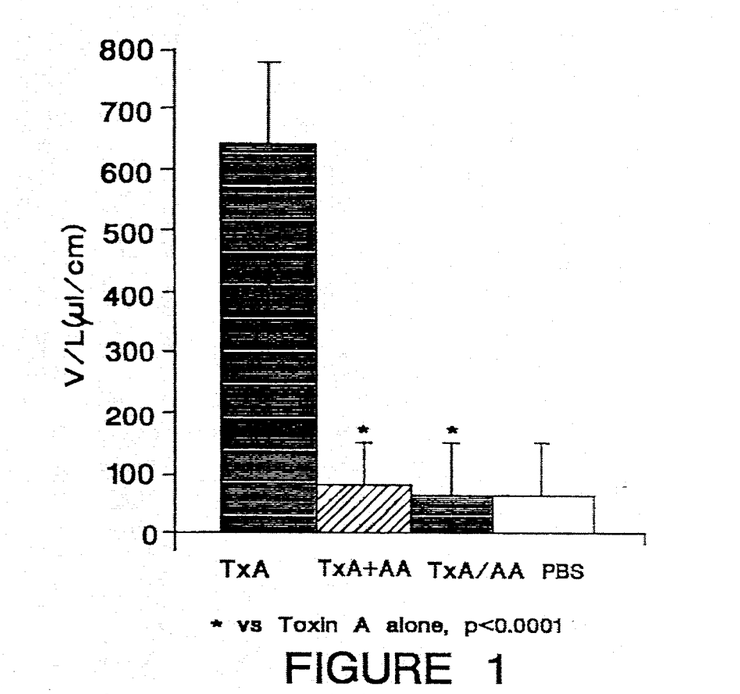
FIG. 1 is a graph illustrating the effects of Aristolochic Acid on *C. difficile* toxin A in rabbit ileum.
Figure 2:
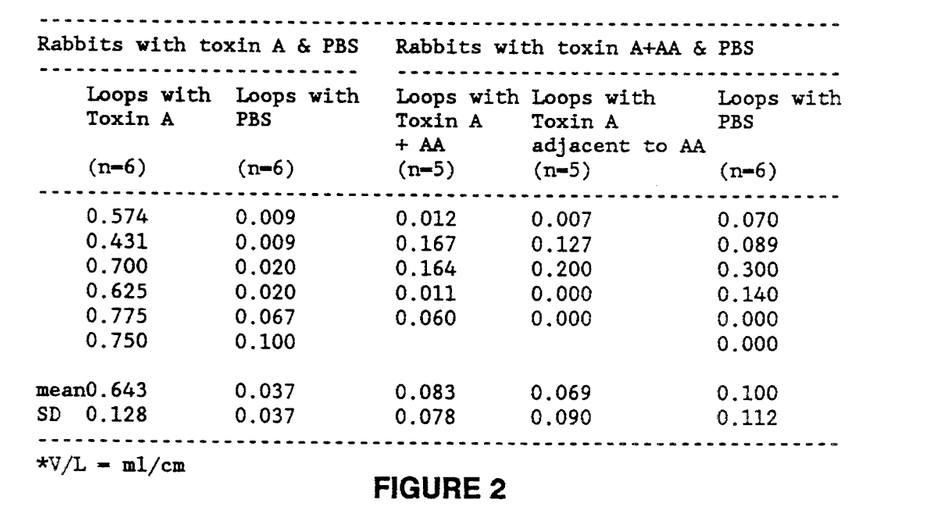
FIG. 2 is a chart illustrating the effects of Aristolochic Acid on *C. difficile* toxin A in rabbit ileal ligated loops.

The toxin A 10 μg/segment hemorrhagic inflammatory fluid secretion was significantly inhibited by $10^{-5}$M AA, a phospholipase $A_2$ inhibitor. AA provided an 87% inhibition, (p<0.0001, n=6). The secretory effect of toxin A was also inhibited in ligated segments adjacent to those with AA (89% inhibition, p≦0.0001, n=6). The results of these tests are illustrated in the graph of FIG. 1 and the chart of FIG. 2.

Figure 3:
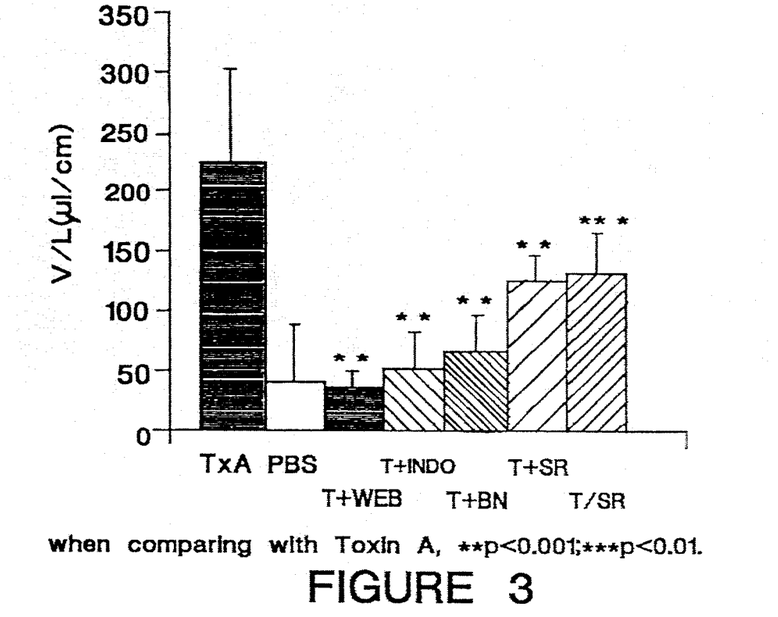
FIG. 3 is a graph illustrating the effects of PAF inhibitors (BN, WEB, SR) and indomethacin on *C. difficile* toxin A in rabbit ileum.
Figure 4:
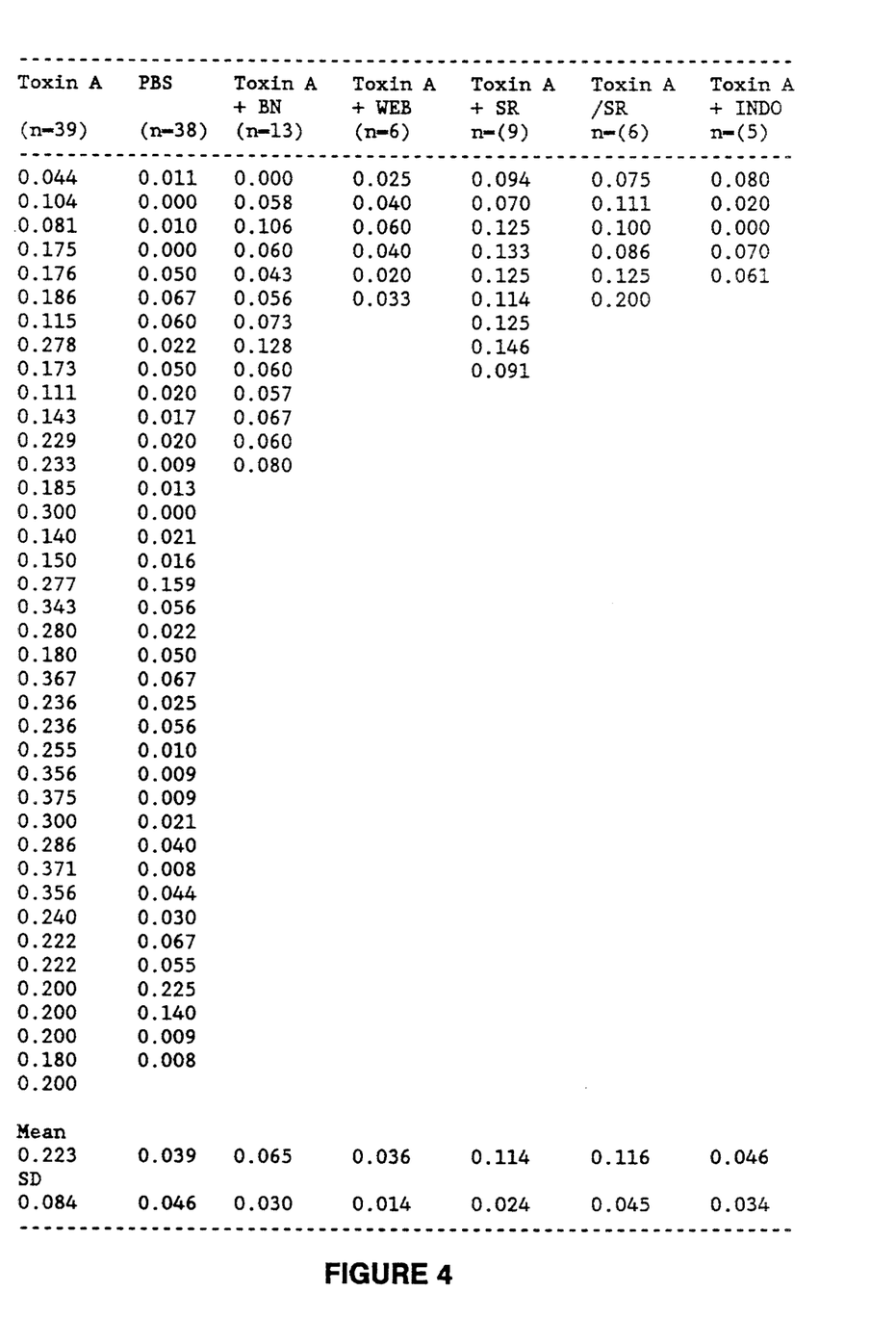
FIG. 4 is a chart illustrating the effects of PAF inhibitors (BN, WEB, SR) or indomethacin on *C. difficile* toxin A in ligated rabbit ileal loops.

The PAF inhibitors, BN ($10^{-4}$M and $10^{-5}$M), WEB (≧$10^6$M) or the cyclooxygenase inhibitor, INDO ($10^5$M), both significantly inhibited the secretory effects of toxin A in ligated but not adjacent rabbit intestinal segments (71% inhibition for BN; 84% for WEB; 79% for INDO; all p<0.0001) as noted in FIGS. 3 and 4. illustrate the test results using p factors of <0.001 and <0. SR gave a reduction of 49% (p<0.001) in the same loops and a reduction of 48% (p<0.01) in the adjacent loops.

Figure 5:
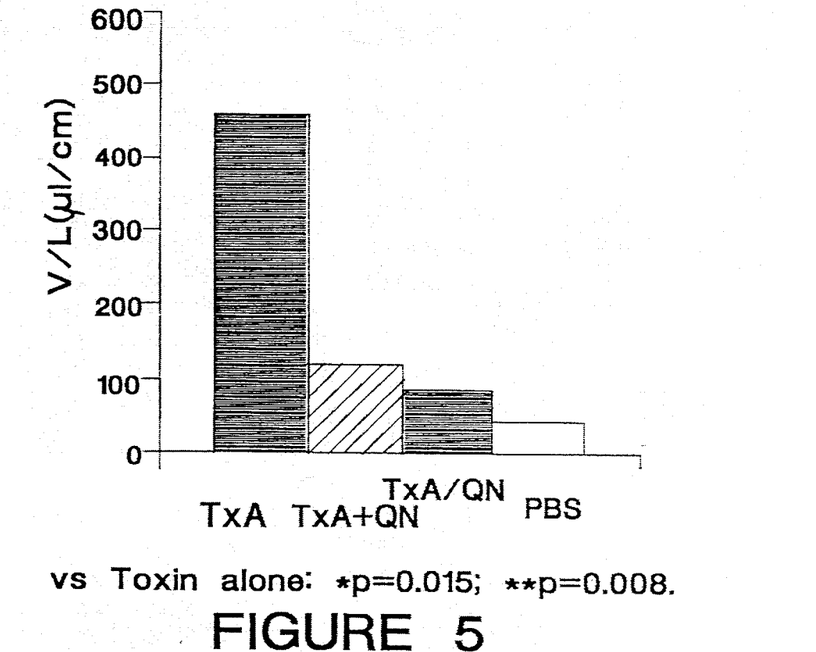
FIG. 5 is a graph illustrating the effects of Quinacrine on *C. difficile* toxin A in rabbit ileum.
Figure 6:
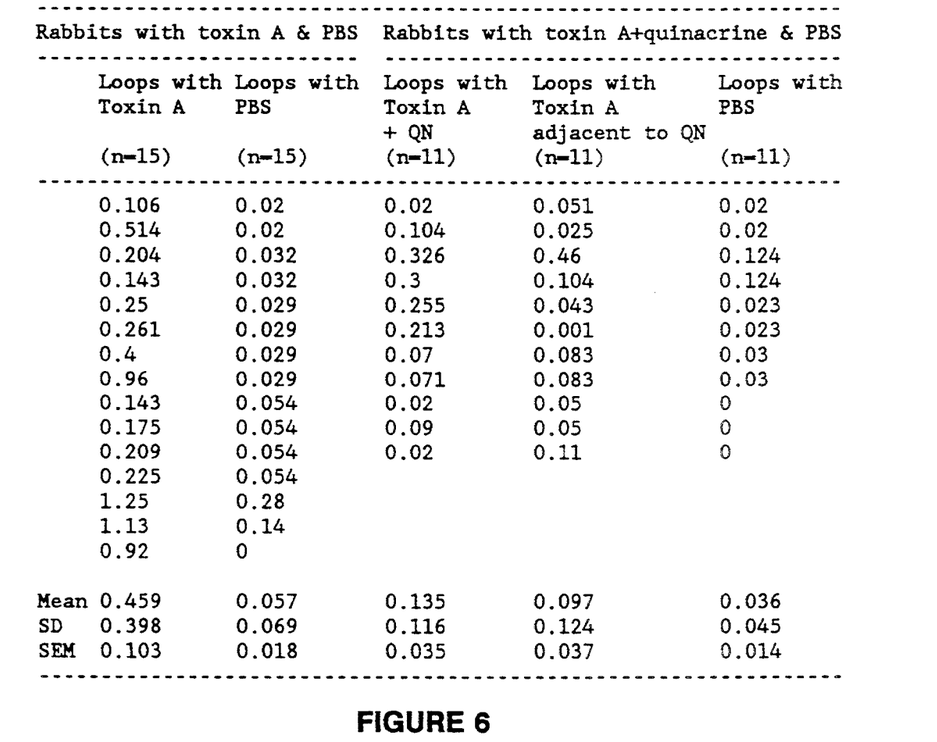
FIG. 6 is a chart illustrating the effects of Quinacrine on *C. difficile* toxin A in ligated rabbit ileal loops.

The secretory effects of C. difficile toxin A with ligated ileal segments were significantly inhibited by phospholipase $A_2$ inhibitor, QN (p<0.05), in both the same or the adjacent loops with toxin A. The test results where p<0.015 and p<0.008 are illustrated in FIGS. 5 and 6.

The phospholipase $A_2$ pathway is involved in the secretory responses to C. difficile toxin A, via the subsequent generation of prostaglandin and/or PAF. The prostaglandin is decreased by the phospholipase The generation of prostaglandin is reduced by the $PLA_2$ or cyclooxygenase inhibitors.

Figure 10:
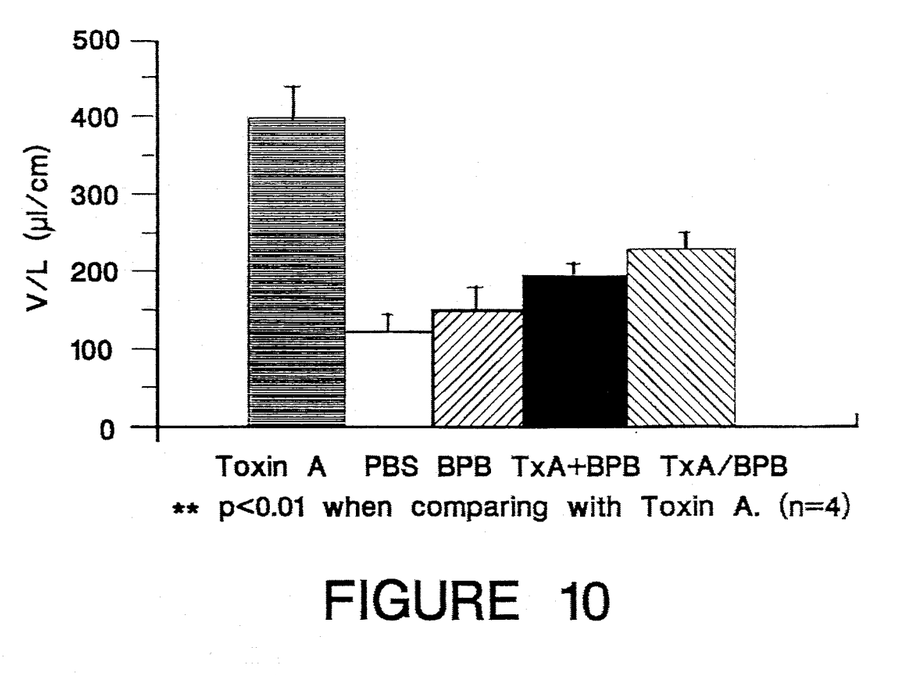
FIG. 10 is a graph illustrating the effects of bromophenacyl bromide on *C. difficile* toxin A in rabbit ileum.

The effects of BPB on the C. difficile toxin A are illustrated in FIG. 10, where p<0.01 and n=4.

The numeric results of the experiments with BN, INDO and WEB 14 are illustrated in Table I.

TABLE 1

Results for Studies of Inhibition of C. diff Toxin A induced Secretion in Rabbits' Loops by PAF and Cyclooxygenase Inhibitors (Vol/Length ratios, μl/cm)

| Rabbit | Toxin | PBS | BN vs Toxin | | INDO | WEB vs Toxin | |
|---|---|---|---|---|---|---|---|
| | | | $10^{-4}$ | $10^{-5}$ | $10^{-5}$ | $10^{-5}$ | $10^{-6}$ |
| 1(2.1 kg) | 43.5 | 20.0 | | | | | |
| | 104.2 | 8.8 | | | | | |
| 2(2.0 kg) | 81.4 | 12.5 | 58.3 | | 19.6 | | |
| | 175.0 | 0.0 | 106.4 | | 0.0 | | |
| 1(2.0 kg) | 175.9 | 20.8 | | | | | |
| | 186.1 | 15.6 | | | | | |
| | 114.8 | | | | | | |
| 2(2.2 kg) | 277.8 | 159.1 | 59.5 | 127.5 | 69.8 | | |
| | 172.8 | 55.6 | 42.6 | 59.5 | 61.0 | | |
| 1(1.6 kg) | 111.1 | 22.2 | | 57.1 | | | |
| | 142.9 | 50.0 | | 66.7 | | | |
| | 228.6 | | | | | | |
| | 233.3 | | | | | | |
| 2(2.1 kg) | 184.6 | 66.7 | | | | 60.0 | 54.5 |
| | 300.0 | 25.0 | | | | 40.0 | 40.0 |
| 1(2.0 kg) | 140.0 | 10.0 | | | | | |
| | 150.0 | 9.1 | | | | | |
| 2(2.1 kg) | 276.6 | 9.1 | 55.6 | 60.0 | | | |
| | 342.9 | 21.3 | 72.7 | 80.0 | | | |
| 3(2.2 kg) | 280.0 | 40.0 | | | | 20.0 | 107.7 |
| | 180.0 | 8.3 | | | | 33.3 | 83.3 |
| Mean | 185.8 | 30.8 | 65.9 | 75.1 | 37.6 | 38.3 | 71.4 |
| SD | 77.9 | 36.9 | 22.1 | 27.0 | 33.3 | 16.7 | 36.9 |
| n | 21 | 18 | 6 | 6 | 4 | 4 | 4 |
| % Inhibition | | | 77.4 | 71.4 | 95.6 | 95.2 | 73.8 |
| p | | <0.001 | 0.001 | 0.002 | 0.001 | 0.001 | 0.009 |

| | Final comparison | | | | |
|---|---|---|---|---|---|
| | Toxin | PBS | BN | WEB | INDO |
| Mean | 185.8 | 30.8 | 70.5 | 62.5 | 37.6 |
| SD | 77.9 | 36.9 | 24.0 | 31.2 | 33.3 |
| % Inhibition | | | 74.4 | 79.5 | 95.6 |
| p | | | <0.001 | <0.001 | 0.001 |

The hemorrhagic fluid secretion caused by *Clostridium difficile* is significantly blocked by two Platelet Activating Factor (PAF) inhibitions, BN 52021 ($10^4$M) or WEB 2170 ($\leq 10^6$M) or by the cyclooxygenase inhibitor indomethacin ($10^{-5}$M); inhibition was 62% with BN52021, 74% for WEB 2170, 65% for indomethacin, all $p<0.05$). PAF inhibitors, alone or in combination with cyclooxygenase inhibitors, provide a means to block the common and often severe antibiotic-associated diarrhea and colitis caused by *Clostridium difficile*.

EXPERIMENT II

T84 cells, a human intestinal epithelial cell line, were grown, passaged, then grown on the 4-well LAB-TEK tissue culture chamber slides (Nunc, Inc., Naperville, Ill.) to confluency. *C. difficile* toxin A 0.7 µg/well (1 ml, final concentration 0.7 µg/ml) alone was placed onto a T84 cell monolayer. Additional cell monolayers were applied with equal concentration of toxin A in combination with:

1 ml BN ($10^{-4}$M),
1 ml WEB ($10^{-4}$M)
1 ml AA ($5\times10^{-4}$M)
1 ml QN ($5\times10^{-4}$M)
1 ml BPB ($10^{-4}$M)
1 ml INDO ($10^{-4}$M)

Cell monolayers were prepared with toxin A 0.7 µg (0.5 ml of 1.4 µg/ml). Additional cells were prepared with the same toxin A concentration in combination with:

0.5 ml BN ($2\times10^{-4}$M)
0.5 ml WEB ($2\times10^{-4}$M) or
0.5 ml AA ($10^{-4}$M)
0.5 ml QN ($10^{-3}$M)
0.5 ml BPB ($2\times10^{-4}$M)
0.5 ml INDO ($2\times10^{-4}$M)

After eight (8) hours incubation, the cell-coated chamber slides were rinsed in PBS and fixed for 15 minutes at room temperature in 3.7% formaldehyde. The slides were rinsed again in PBS, permeabilized for five (5) minutes in 20° C. acetone, air dried, stained with rhodamine-labeled phalloidin for 30 minutes at room temperature in the dark, rinsed twice in PBS and kept in the dark at 4° C. Cells were then examined and photographed using an inverted Olympus fluorescence microscope. To compare the pattern of labeling between toxin-treated and PAF inhibitors or phospholipase $A_2$ inhibitors or cyclooxygenase inhibitor plus toxin-treated mono-layers, photomicrographs were taken with Kodak 400, daylight slides and exposures were varied to optimize the resulting images.

The destruction by toxin A (0.7 µg/ml) of rhodamine-labeled phalloidin-stained F-actin at the tight junctions of T-84 cell monolayers was inhibited by $5\times10^{-4}$M AA or $10^{-4}$M BPB (n=2–4 experiments each). BN, INDO, WEB, and QN also inhibited the reduction in F-acting staining by toxin A.

EXPERIMENT III

T84 cells, a human intestinal epithelial cell line, were grown, passaged and mounted on collagen-coated microfilters. Transepithelial resistances generated by the ring-mounted monolayers used for these studies ranged from 2600 to 4000Ω cm$^2$.

When the T84 cells grown on the microfilters reached confluence as determined by phase microscopy and development of a high, stable resistance, toxin A 0.02 µg (10 µl, final concentration 0.07 µg/ml), or 36 µl QN ($2\times10^{-4}$M, final concentration $2\times10^{-5}$M), or toxin A 0.02 µg plus 36 µl QN($2\times10^{-4}$M) were added into 300 µl tissue culture medium. All above reagents were applied only to the apical (mucosal) surface of the monolayers. Resistance was measured every hour during the first eight hours and then at 10, 12 and 24 hours.

Figure 7:
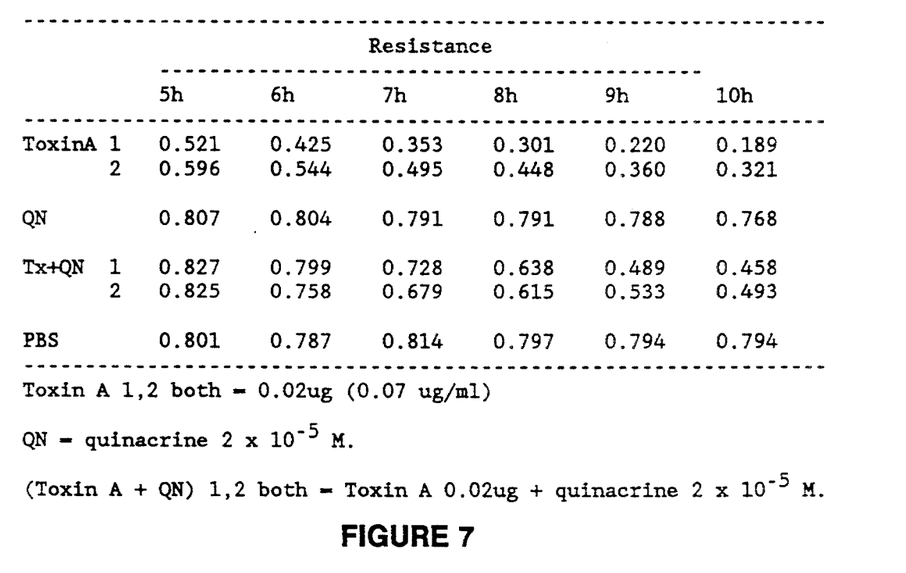
FIG. 7 is a chart illustrating the effects of Quinacrine on *C. difficile* toxin A in T84 cell monolayers.
Figure 8:
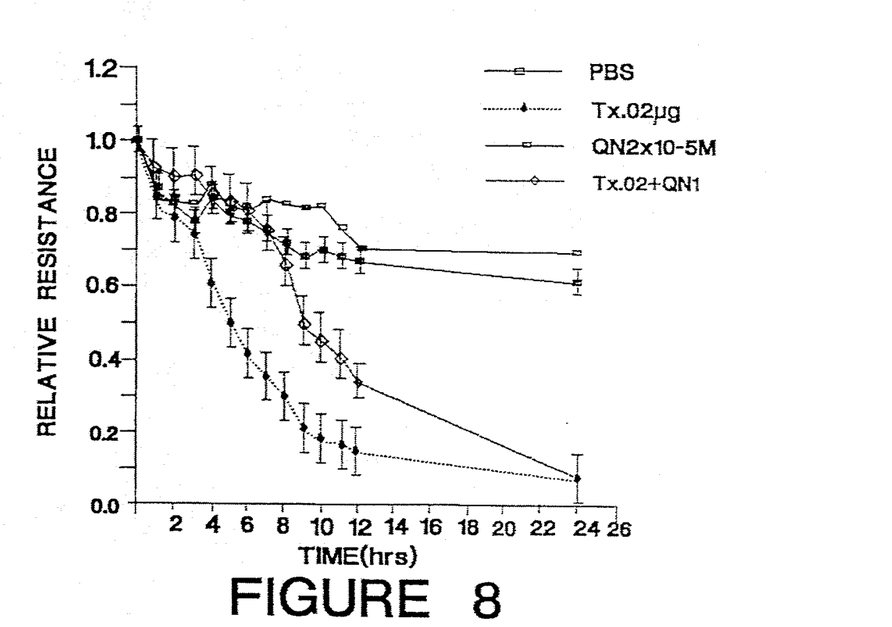
FIG. 8 is a graph illustrating the effects of Quinacrine on *C. difficile* toxin A in T84 cell monolayers.

The results of the QN resistance are shown in FIGS. 7 and 8. Simultaneous administration of QN ($p<0.05$) additionally significantly inhibited tissue resistance in the T84 cell monolayers caused by toxin A at 5–6 hours exposure.

The foregoing PAF inhibitors, BN and SR and Indomethacin, have been found to significantly reduce the enterotoxin Cholera toxin (choleragen) produced by *Vibrio cholerae*, as well as *C. difficile*. Choleragen acts on the epithelial cells in the small intestine to cause secretion of large quantities of isotonic fluid from the mucosal surface. Choleragen is affected by the PAF inhibitors similarly to the toxin A created by *Clostridium difficile*. The Cholera related diarrhea results in massive gastrointestinal fluid loss and saline depletion, acidosis and shock. The ability to control the effects of the diarrhea would allow the body to absorb badly needed fluids, nutrients and medication, and eliminate the further depletion of the body's resources and resulting deficiencies.

EXPERIMENT IV

Cholera toxin, alone and in combination with the inhibitors, BN, SR and indomethacin, were placed in 4–6 cm ligated Ileal segments in 1.5–2.5 kg, male, New Zealand white rabbits. The rabbits were fasted overnight and provided water ad libitum. The animals were anesthetized with an initial intramuscular dose of ketamine (35 mg/kg body weight) and xylazine (5 mg/kg). Ligated rabbit small intestinal segments of approximately 5 cm were made with double ties of umbilical tape. These segments were injected with the following combinations and then returned to the abdominal cavity without separation from the remaining intestine or interruption of the blood supply. After six (6) hours the animals were sacrificed and the fluid volume (milliliters) and length (centimeters) for each loop was measured and a volume to length ratio calculated. Choleragen 10 µg/segment in 1 ml consistently caused severe hemorrhagic inflammatory fluid secretion at 6–8 hours (V/L=0.64±0.13 ml/cm segment, n=6). The molarity (M) indicates the drug concentration in the 1 ml containing the 10 µg/ml choleragen.

Each rabbit was injected with one of the following:
1 ml choleragen in PBS (1 µg/ml)
1 ml PBS (as a control),
1 ml choleragen and BN52021 ($-^4$M and $10^{-5}$M) [BN]
1 ml choleragen and SR27417 ($10^{-5}$ and $10^{-6}$M) [SR]
1 ml choleragen and a combination of BN52021 ($10^{-5}$M) [BN], indomethacin ($10^{-5}$M) [INDO]
0.5 ml choleragen and SR($2\times10^{-5}$M and $2\times10^{-6}$)
0.5 ml choleragen and BN($2\times10^{-5}$M)
0.5 ml choleragen and INDO($2\times10^{-5}$M)

Figure 9:
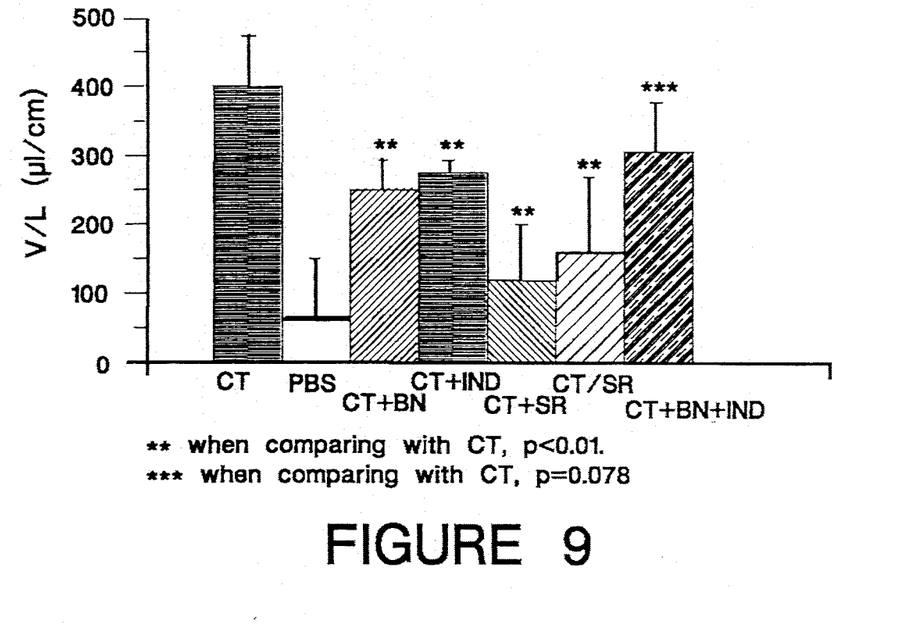
FIG. 9 is a graph illustrating the effects of PAF inhibitors (BN and SR) and indomethacin on cholera toxin in rabbit loops.

The choleragen 1 µg/segment hemorrhagic inflammatory fluid secretion was significantly inhibited by $10_5$–$10^6$M SR27417. SR provided an 86% inhibition when placed in the loop with the toxin, as well as a slightly lesser inhibition when in the loop adjacent to the toxin, (both $p<0.011$), as illustrated in FIG. 9.

The PAF inhibitors, BN ($10^{-4}$M and $10^{-5}$M), and INDO ($10^5$M), both significantly inhibited the secretory effects of toxin A in ligated intestinal segments (44% inhibition for BN; 38% for INDO, both $p<0.01$).

What is claimed is:

1. The method of blocking hemorrhagic fluid secretion caused by *Clostridium difficile* toxin A in ligated intestinal segments, comprising administering an effective amount to reduce hemorrhagic fluid secretion of a Platelet Activating Factor inhibitor selected from the group consisting of BN52021, WEB 2170 and SR27417.

2. The method of claim 1 wherein said Platelet Activating Factor inhibitor is administered by injection.

3. The method of claim 1 wherein said Platelet Activating Factor inhibitor is a tablet.

4. The method of blocking hemorrhagic fluid secretion caused by *Clostridium difficile* toxin A in ligated intestinal segments, comprising administering an effective amount to reduce hemorrhagic fluid secretion of a cyclooxygenase inhibitor.

5. The method of claim 4 wherein said cyclooxygenase inhibitor is administered by injection.

6. The method of claim 4 wherein said cyclooxygenase inhibitor is a tablet.

7. The method of claim 4 wherein said cyclooxygenase inhibitor is indomethacin.

8. The method of blocking hemorrhagic fluid secretion caused by *Clostridium difficile* toxin A in ligated intestinal segments, comprising the step of treating said intestinal segments with the combination of the cyclooxygenase inhibitor indomethacin and at least one Platelet Activating Factor antagonist from the group consisting of WEB 2170, SR 27417 and BN 52021.

9. The method of claim 8 wherein said combination is administered by injection.

10. The method of claim 8 wherein said combination is a tablet.

* * * * *